United States Patent
Qiu (10) Patent No.: US 10,426,903 B2
(45) Date of Patent: Oct. 1, 2019

(54) AUTOMATIC TRIGGER MODULE AND ELECTRONIC CIGARETTE THEREOF

(71) Applicant: Joyetech Europe Holding GmbH, Zug (CH)

(72) Inventor: Weihua Qiu, Jiangsu (CN)

(73) Assignee: JOYETECH EUROPE HOLDING GMBH, Zug (CH)

(*) Notice: Subject to any disclaimer, the term of this patent is extended or adjusted under 35 U.S.C. 154(b) by 93 days.

(21) Appl. No.: 15/692,668

(22) Filed: Aug. 31, 2017

(65) Prior Publication Data

US 2018/0056016 A1 Mar. 1, 2018

(30) Foreign Application Priority Data

Aug. 31, 2016 (CN) .......................... 2016 1 0797795

(51) Int. Cl.
| | | |
|---|---|---|
| *A24F 11/00* | (2006.01) | |
| *A24F 47/00* | (2006.01) | |
| *A24F 13/00* | (2006.01) | |
| *A24F 17/00* | (2006.01) | |
| *A24F 25/00* | (2006.01) | |
| *A61M 15/06* | (2006.01) | |
| *A61M 11/04* | (2006.01) | |
| *A61M 16/00* | (2006.01) | |
| *H05B 3/00* | (2006.01) | |

(52) U.S. Cl.
CPC .......... *A61M 15/06* (2013.01); *A24F 47/002* (2013.01); *A61M 11/042* (2014.02); *A61M 2016/0018* (2013.01); *A61M 2016/0039* (2013.01); *A61M 2205/8206* (2013.01); *H05B 3/0014* (2013.01)

(58) Field of Classification Search
CPC ............................. A24F 47/008; A24F 47/002
USPC ................................................... 131/329, 328
See application file for complete search history.

(56) References Cited

U.S. PATENT DOCUMENTS

| | | | |
|---|---|---|---|
| 2014/0020696 A1* | 1/2014 | Liu ....................... | A24F 47/002 131/329 |
| 2015/0027473 A1* | 1/2015 | Graf ....................... | F22B 1/288 131/329 |
| 2015/0144148 A1* | 5/2015 | Chen ..................... | A24F 47/008 131/329 |
| 2015/0157054 A1* | 6/2015 | Liu ....................... | A24F 47/008 131/329 |
| 2015/0189919 A1* | 7/2015 | Liu ....................... | A24F 47/008 131/329 |

(Continued)

*Primary Examiner* — Abdullah A Riyami
*Assistant Examiner* — Thang H Nguyen
(74) *Attorney, Agent, or Firm* — Novick, Kim & Lee, PLLC; Allen Xue (57) ABSTRACT

Provided is an automatic trigger module for electronic cigarette, comprising a circuit board, a sensor and a sealing seat. The sensor is provided on the circuit board, and the circuit board is provided with a first vent hole at the position corresponding to the sensor and a first connection. The sealing seat is provided with a second vent hole. The circuit board and the sensor are arranged on the sealing seat, with the sensor being inserted into the second vent hole. Therefore, it is an object of the present disclosure to solve the problem of resource waste due to the unreplaceable automatic trigger module in the electronic cigarette of the prior art. The present disclosure also provides an electronic cigarette using the automatic trigger module.

14 Claims, 6 Drawing Sheets

(56) References Cited

U.S. PATENT DOCUMENTS

| | | | |
|---|---|---|---|
| 2015/0196055 A1* | 7/2015 | Liu | A24F 47/008 |
| | | | 131/329 |
| 2015/0272214 A1* | 10/2015 | Giller | A24F 47/002 |
| | | | 131/329 |
| 2016/0073694 A1* | 3/2016 | Liu | H05B 3/40 |
| | | | 131/329 |
| 2016/0198767 A1* | 7/2016 | Verleur | H05B 1/0202 |
| | | | 392/386 |
| 2016/0366946 A1* | 12/2016 | Murison | A24F 15/12 |
| 2017/0099878 A1* | 4/2017 | Murison | H02J 7/0044 |
| 2017/0169679 A1* | 6/2017 | Johnson | G08B 13/19695 |
| 2018/0184722 A1* | 7/2018 | Murison | F04B 43/046 |
| 2018/0340350 A1* | 11/2018 | Johnson | G08C 23/02 |
| 2019/0000147 A1* | 1/2019 | Koc | A61M 15/06 |

* cited by examiner

AUTOMATIC TRIGGER MODULE AND ELECTRONIC CIGARETTE THEREOF

CROSS REFERENCE TO RELATED APPLICATIONS

This application claims priority to Chinese Patent Application No. CN201610797795.2, filed on Aug. 31, 2016, the entirety of which is incorporated by reference herein.

FIELD

The present disclosure relates to the field of simulated smoking, and more particularly, to an automatic trigger module and an electronic cigarette using the same.

BACKGROUND

Box-style electronic cigarette is a kind of electronic cigarette, which is typically larger in size than the rod-shaped small electronic cigarette. Box-style electronic cigarette can have a case-like housing in various shapes, such as column, cuboid, irregular shape, and so on. Although electronic cigarettes that adopt sensors to realize automatic activating function have been existing on the market, the sensors are not detachable. Due to the short life of the sensor itself, once the sensor is broken, the electronic cigarette loses its function of automatic activating and is thus no longer good for use, causing a considerable waste.

SUMMARY

It is an object of the present disclosure to solve the defects in the prior art by providing an automatic trigger module and an electronic cigarette using the same.

The technical solutions of the automatic trigger module for an electronic cigarette of the present disclosure are as follows:

An automatic trigger module for an electronic cigarette can comprise a sensor, a circuit board and a sealing seat. The sensor can comprise a first end and a second end which opposite to each other. The circuit board can define a first vent hole configured to communicate with the first end and a first connection. The sealing seat can define a second vent hole configured to communicate with the second end. The first end can be located on the circuit board, and the second end of the sensor can be arranged in the second vent hole.

In one embodiment, the sealing seat can define a via hole corresponding to the first connection.

In one embodiment, the first connection can be a contact dot, a contact post or a contact sheet.

The automatic trigger module disclosed in the present disclosure has a function to activate the electronic cigarette. When the first end and the second end in different air pressure states, the sensor can generate a high potential signal which is then transmitted to the circuit board through the first connection, and then the circuit board can activate the electronic cigarette according to the high potential signal. Therefore, the application of the automatic trigger module on the electronic cigarette can make the electronic cigarette activate automatically. In addition, the integral structure design allows the possibility of disassembly during practical applications. Further, the use of the sealing seat can protect the sensor, and can also solve the sealing problem during assembling. The automatic trigger module provided in the present disclosure has good seal performance, and can be assembled conveniently.

The technical solutions applied in the electronic cigarette with the automatic trigger module in the present disclosure are as follows:

An electronic cigarette can comprise an automatic trigger module and a control board. The automatic trigger module can comprise a sensor, a circuit board and a sealing seat. The sensor can comprise a first end and a second end which opposite to each other. The circuit board can comprise a first vent hole configured to communicate with the first end and a first connection. The sealing seat can define a second vent hole configured to communicate with the second end. The first end can be located on the circuit board, and the second end can be located in the second vent hole. The circuit board can comprise a second connection, wherein the automatic trigger module is detachably connected to the control board, and when the automatic trigger module is connected to the control board, the first connection and the second connection contact with each other to realize a transmission of signal.

In one embodiment, the sealing seat can define a via hole corresponding to the first connection.

In one embodiment, the first connection can be a contact dot, a contact post or a contact sheet.

In one embodiment, the second connection can be a contact dot, a contact post or a contact sheet.

In one embodiment, the electronic cigarette can further comprise an inductive passage and a cigarette holder, wherein one end of the inductive passage communicates with the second vent hole and the other end of the inductive passage communicates with the cigarette holder.

In one embodiment, the electronic cigarette can further comprise a housing which defines a mounting hole for the automatic trigger module to pass through when mounting or removing.

In one embodiment, the electronic cigarette can further comprise a rear cover which defines a receiving cavity configured to receive the automatic trigger module and an air inlet opening corresponding to the first vent hole, wherein the automatic trigger module is received in a space formed by the receiving cavity and the control board.

In one embodiment, the electronic cigarette can further comprise a main support which defines a through hole, wherein the automatic trigger module passes through the through hole and then is detachably connected to the control board.

In one embodiment, the electronic cigarette can further comprise a clamping ring located on the outside of the rear cover, and a clamping slot defined on the wall of the through hole, wherein the rear cover is fixed on the main support through the cooperation of the clamping ring and the clamping slot.

In one embodiment, the electronic cigarette can further comprise an insert block located on the outside of the clamping ring, and an insert block groove defined on the main support, wherein the insert block can be engaged with the insert block groove.

In one embodiment, the electronic cigarette can further comprise a button, wherein the button is a standby power button and/or a safety protection button.

The electronic cigarette provided in the present disclosure adopts the automatic trigger module which is detachably connected to the control board. Accordingly, the automatic trigger module of the electronic cigarette is replaceable, which overcomes the problems in the prior art, and is suitable for wide application. Specifically, the automatic trigger module of the electronic cigarette herein is provided with the first connection and the via hole, and the control board is provided with the second connection which can pass through the via hole and then abut against the first connection. The automatic trigger module is detachably connected to the control board through the cooperation of the second connection and the via hole. The signal connection and electrical connection between the automatic trigger module and the control board are realized through the first connection and the second connection contacting with each other. When the user needs to detach the automatic trigger module, he or she just needs to withdraw the second connection from the via hole. Therefore, the automatic trigger module of the electronic cigarette according to the present disclosure is detachable, and can be easily detached and replaced.

BRIEF DESCRIPTION OF THE DRAWINGS

The drawings are provided for further understanding of the disclosure and constitute a part of the specification, and are used, together with the following detailed description, to explain the disclosure, and should not be construed as a limitation for the disclosure. In the drawings.

Figure 1:
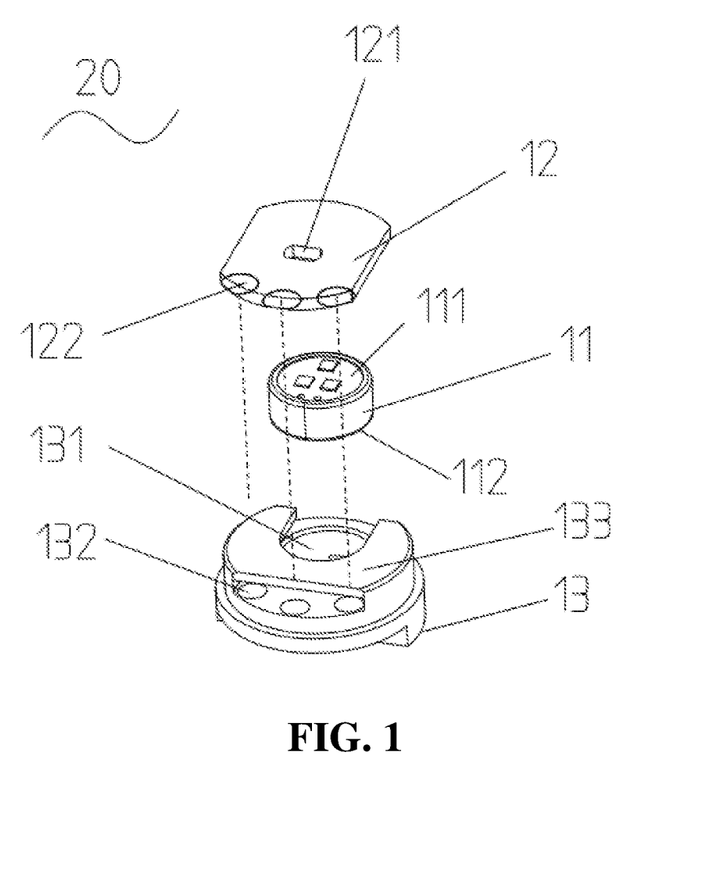
FIG. 1 is an exploded view of an automatic trigger module for electronic cigarette according to an embodiment of the present disclosure.

trigger module 20 can include a circuit board 12, a sensor 11, and a sealing seat 13. The circuit board 12 is a wiring board with the sensor 11 assembled thereon, which can be a printed circuit board (PCB), or a printed circuit board assembly (PCBA), or the like. The circuit board 12 is mainly configured to carry the sensor 11 and conduct the circuit of the sensor 11. The sensor 11 is fixedly connected to the circuit board 12. In one embodiment, the sensor 11 is fixedly connected to the circuit board 12 by soldering. The outer side of the sensor 11 is surrounded by the sealing seat 13 to avoid the interference of airflow. In this embodiment, the sealing seat 13 is made of silicone rubber. It can be appreciated that, the sealing seat 13 can be made of other materials with good insulation and sealing properties, such as thermoplastic polyurethanes (TPU), thermoplastic vulcanizate (TPV) and ceramic. The circuit board 12 includes a first connection 122 connected to a second connection 211 of the electronic cigarette, so as to achieve transmission of signals and power.

This embodiment is specifically implemented as follows: the sensor 11 includes a first end 111 and a second end 112 which are opposite to each other. The first end 111 is located on the circuit board 12, and the circuit board 12 defines a first vent hole 121 corresponding to the first end 111. The circuit board 12 includes a first connection 122 staggered from the sensor 11. The sealing seat 13 defines a second vent hole 131 corresponding to the sensor 11 and a via hole 132 on the side of the second vent hole 131. The circuit board 12 and the sensor 11 are integrally connected together and positioned at the sealing seat 13. The first connection 122 corresponds to the via hole 132, and the second end 112 is inserted into the second vent hole 131.

In one embodiment, the sealing seat 13 has an approximately cylindrical structure. The second vent hole 131 is defined in the sealing seat 13 and pass through two opposite end of the sealing seat 13. The sensor 11 is received in the second vent hole 131.

In one embodiment, the via hole 132 is defined in the sealing seat 13, and the second connection 211 passes through the via hole 132 and then abuts against the first connection 122.

NAME AND REFERENCE NUMERAL OF COMPONENTS

| | | | |
|---|---|---|---|
| Sensor: 11 | Circuit Board: 12 | Sealing Seat: 13 | First Vent Hole: 121 |
| First Connection: 122 | Second Vent Hole: 131 | Via Hole: 132 | Sheltering Sheet: 133 |
| Control Board: 21 | Second Connection: 211 | Cigarette Holder: 22 | Cigarette Holder Seat: 23 |
| Air Adjusting Ring: 24 | Clamping Slot: 25 | Button: 26 | Battery: 27 |
| Adjusting Button: 28 | Clamping Ring: 29 | Automatic Trigger Module: 20 | Insert Block: 31 |
| Insert Block Groove: 32 | Connecting Member: 33 | Smoke Pipe: 34 | Air Inlet Pipe: 35 |
| Atomizer Head: 36 | Electrode Tip: 37 | Air Inlet Passage: 38 | Inductive Passage: 39 |
| First end: 111 | Rear Cover: 42 | Air Inlet Opening: 43 | Housing: 44 |
| Mounting Hole: 45 | Main Support: 46 | Second End: 112 | Through Hole: 48 |

DETAILED DESCRIPTION

Specific embodiments of the present disclosure will be described in detail below with reference to the drawings. It should be understood that the specific embodiments described herein are for the purpose of illustration and explanation of the present disclosure, and are not intended to limit the disclosure.

Example 1

FIG. 1 illustrates a first embodiment of an automatic trigger module 20 for an electronic cigarette. The automatic In one embodiment, the sealing seat 13 further includes a sheltering sheet 133 located between the circuit board 12 and the sealing seat 13. The sheltering sheet 133 defines a through-hole communicating with the second vent hole 131 and is sleeved at the outside of the sensor 11.

In one embodiment, the sheltering sheet 133 is made of sealing materials, such as rubber and the like, to prevent the sensor 11 from shaking and avoid interference with external airflow.

It can be appreciated that, the sheltering sheet 133 can be integrally formed with the sealing seat 13 and be made of the same material as the sealing seat 13.

In this embodiment, the automatic trigger module 20 has three first connections 122. One of the first connections 122 is connected with the corresponding second connection 211 to realize the signal transmission, and the other two first connections 122 are respectively connected with the corresponding second connections 211 to realize the power transmission. It can be appreciated that, in other embodiments, the automatic trigger module 20 has an internal power source, thus the first connections 122 configured for power transmission can be omitted. It can be appreciated that, the number of the first connections 122 can be adjusted according to the types of signal transmission method. In other embodiments, the number of the first connections 122 for signal transmission also can be two or more.

In this embodiment, the first connections 122 are provided as contact dots. It can be appreciated that, in other embodiments, the first connections 122 can be provided in other ways, such as contact posts or contact sheets.

Correspondingly, the second connections 211 in this embodiment are provided as contact posts. It can be appreciated that, in other embodiments, the second connections 211 can be provided in other ways, such as contact dots or contact sheets. The setting ways of the first connections 122 and the second connections 211 are not limited, as long as the first connections 122 and the second connections can realize the transmission of signal and power through contacting with each other.

In this embodiment, the automatic trigger module 20 is detachably mounted on the electronic cigarette through the cooperation of the second connection 211 and the via hole 132. It can be appreciated that, in other embodiments, the automatic trigger module 20 can be detachably mounted on the electronic cigarette through other connection ways. For example, the electronic cigarette defines an engaging slot, and an engaging member corresponding to the engaging slot is formed on the automatic trigger module 20. The automatic trigger module 20 can be detachably mounted on the electronic cigarette through the cooperation of the engaging slot and the engaging member.

The automatic trigger module 20 disclosed in this embodiment has a function to activate the electronic cigarette. The first end 111 communicates with the external air through the first vent hole 121, so that the first end 11 is in the atmospheric pressure state. The second end 112 communicates with cigarette holder 22 through the second vent hole 131. When the user inhales, the air at the second end 112 can be sucked off through the second vent hole 131 and the cigarette holder 22, causing the second end 112 of the sensor 11 in a negative pressure state. When the first end 111 and the second end 112 in different air pressure states, the sensor 11 can generate a high potential signal which is then transmitted to the circuit board 12 through the first connection 122, and then the circuit board 12 can activate the electronic cigarette according to the high potential signal. Therefore, the application of the automatic trigger module 20 on the electronic cigarette can make the electronic cigarette activate automatically. In addition, the integral structure design allows the possibility of disassembly during practical applications. Further, the use of the sealing seat 13 can protect the sensor 11, and can also solve the sealing problem during assembling. The automatic trigger module 20 provided in the present disclosure has good seal performance, and can be assembled conveniently.

Example 2

Figure 2:
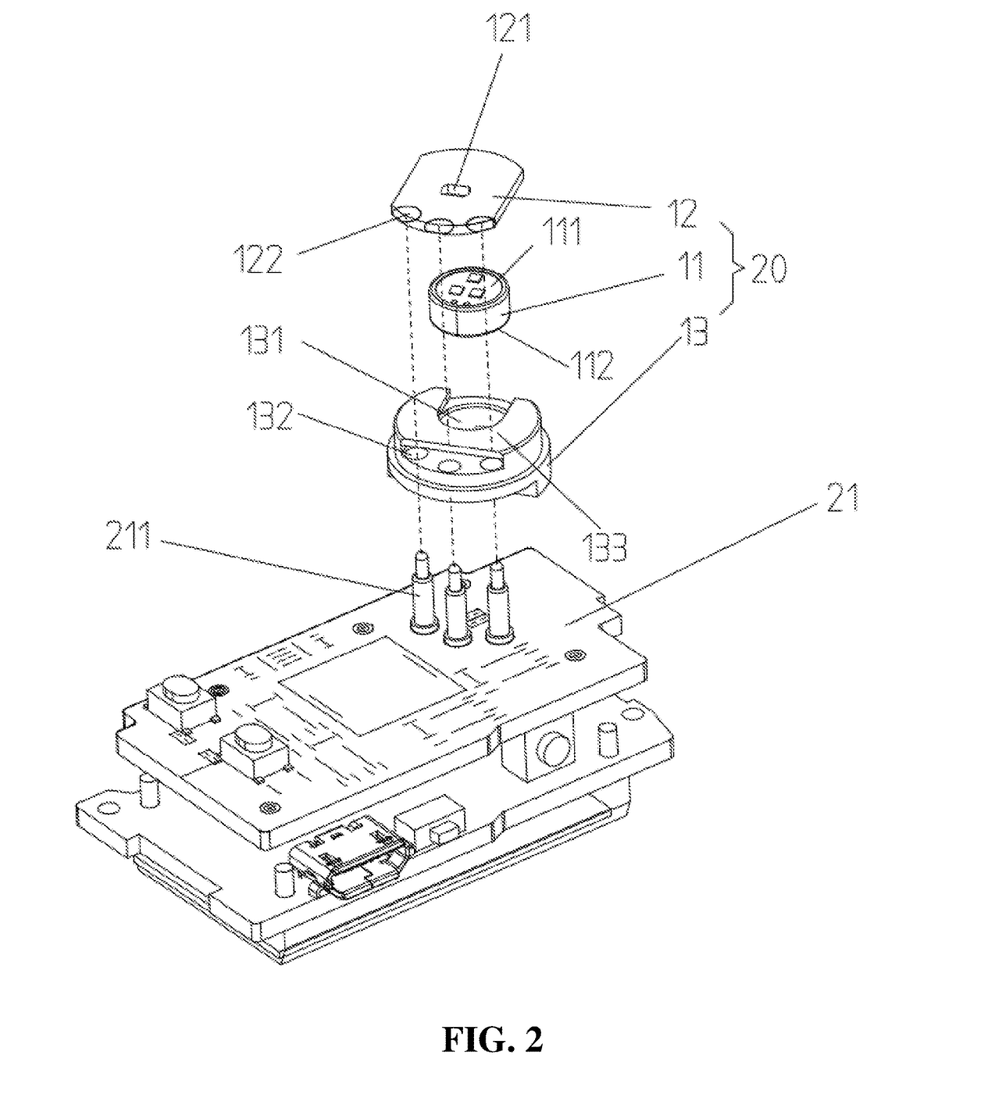
FIG. 2 is a schematic diagram showing the mounting relationship between the automatic trigger module of the electronic cigarette and the control board according to an embodiment of the present disclosure.

As shown in FIGS. 1 to 7, this embodiment discloses an electronic cigarette using the automatic trigger module 20 according to the first embodiment. In addition to the automatic trigger module 20 described above, the electronic cigarette further comprises a cigarette holder 22, a battery assembly (not labeled), an atomizing assembly (not labeled), and a control board 21. In this embodiment, the control board 21 is a PCBA. The second connection 211 is located in the PCBA corresponding to the via hole 132. The automatic trigger module 20 is detachably connected to the PCBA. Specifically, when the via hole 132 is located in the sealing seat 13, the second connection 211 can pass through the via hole 132 and then abuts against the first connection 122, so as to realize the electrically connection and signal connection between the automatic trigger module 20 and the control board 21. It can be appreciated that the via hole 132 can be omitted. The automatic trigger module 20 can be detachably connected to the control board 21 in other ways, as long as the first connection 122 and the second connection can realize the signal transmission and the power transmission when the automatic trigger module 20 is mounted on the control board 21. As shown in FIG. 2, in this embodiment, the second connection 211 is provided as contact post, and the number of the second connection 211 is three. The second connections 211 are spaced from each other, wherein the spacing can be 1 micrometer (mm) to 8 mm. It can be appreciated that, the number of the second connections 211 and the spacing therebetween are not limited herein, but depending on the actual transmission requirements and assembly requirements.

The structure and mechanism for forming the pressure difference in the automatic trigger module 20 are as follows: the electronic cigarette includes an inductive passage 39. One end of the inductive passage 39 communicates with the second vent hole 131, and the other end of the inductive passage 39 communicates with the cigarette holder 22. In this embodiment, the electronic cigarette further includes an air flow passage communicating between the cigarette holder 22 and an air inlet, and the inductive passage 39 communicates with the cigarette holder 22 through the air flow passage. It can be appreciated that, in other embodiments, the inductive passage 39 can communicate with the cigarette holder 22 directly. The first end 111 communicates with the external air through the first vent hole 121, so that the first end 11 is in a state of normal pressure. The second end 112 of the sensor 11 communicates with cigarette holder 22 through the second vent hole 131 and the inductive passage 39. When the user inhales, the air at the second end 112 can be sucked off through the second vent hole 131, the inductive passage 39 and the cigarette holder 22, causing the second end 112 in a negative pressure state. When the first end 111 and the second end 112 in different air pressure states, the sensor 11 can generate a high potential signal which is then transmitted to the circuit board 12 through the first connection 122 and the second connection 211, and then the circuit board 12 can activate the electronic cigarette according to the high potential signal.

Figure 3:
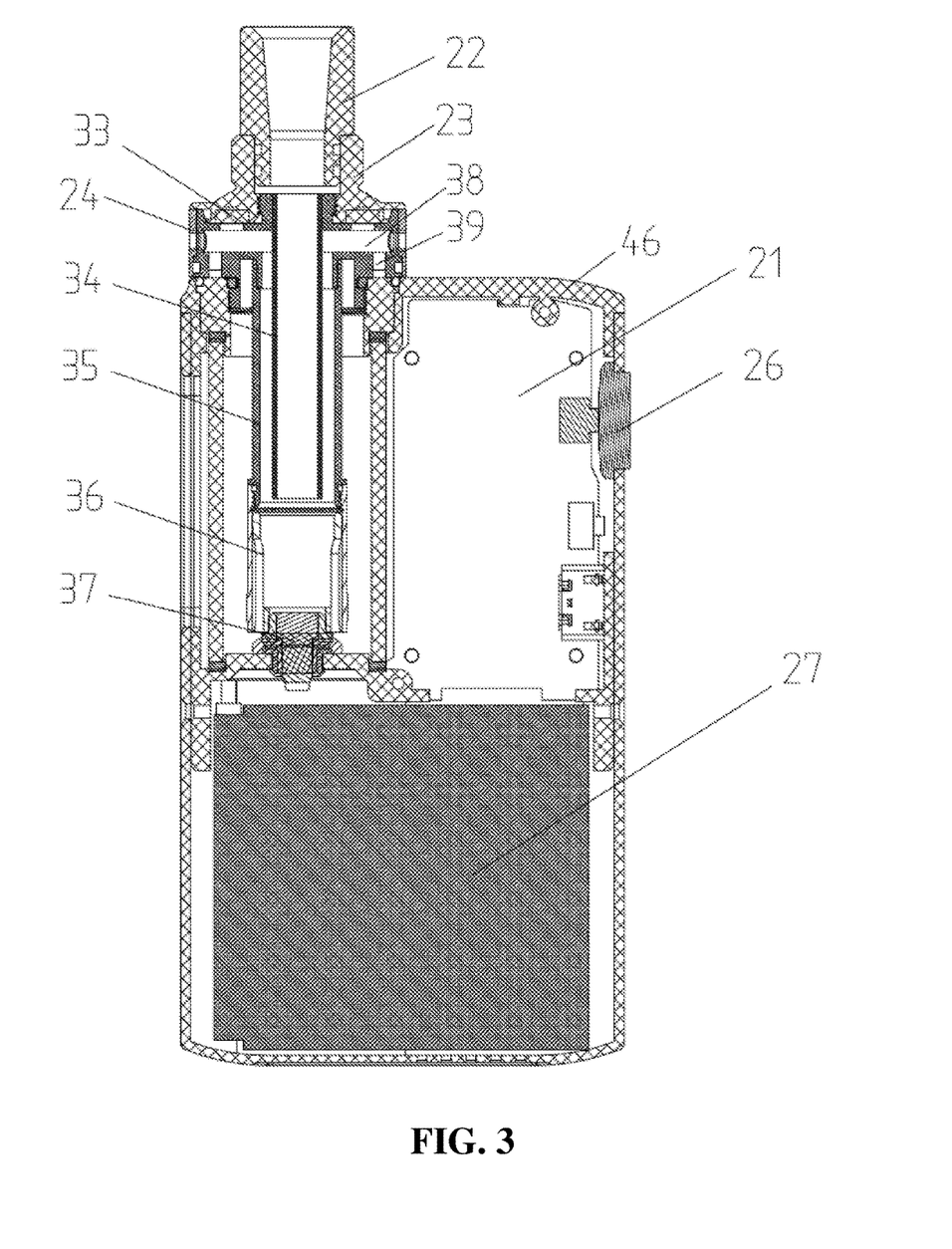
FIG. 3 is a cross-sectional view of the electronic cigarette according to an embodiment of the present disclosure.
Figure 4:
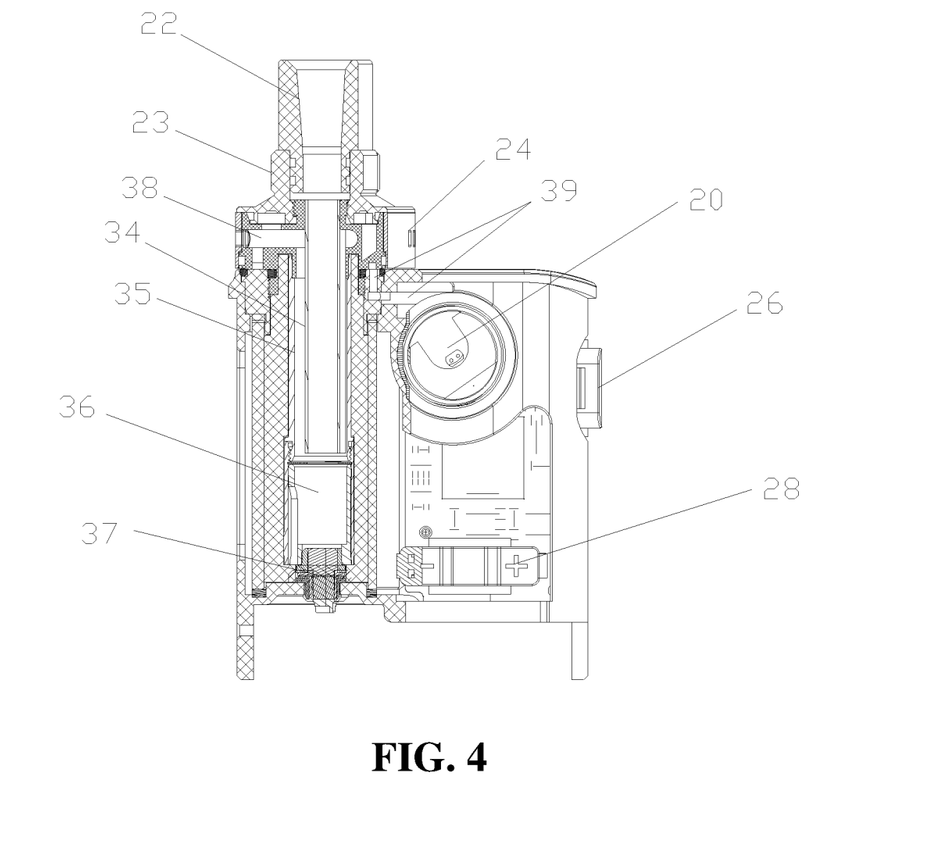
FIG. 4 is a partial half-sectional view of the electronic cigarette according to an embodiment of the present disclosure.
Figure 7:
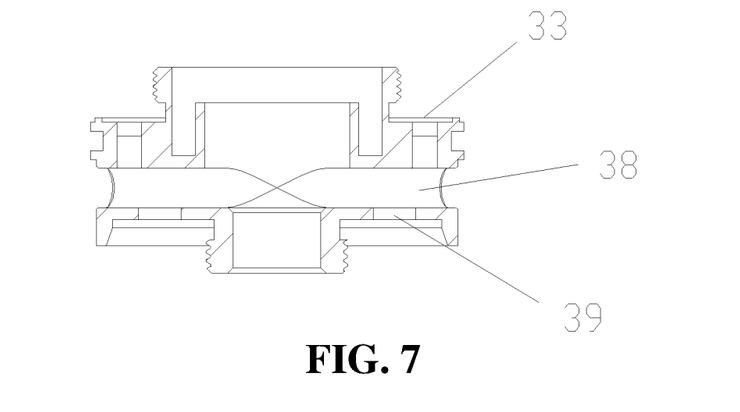
FIG. 7 is a cross-sectional view of a connecting member according to an embodiment of the present disclosure.

Specifically, as shown in FIG. 3, the electronic cigarette further comprises a main support 46. A connecting member 33 is located in the left upper end of the main support 46. A cigarette holder seat 23 and the cigarette holder 22 are located at the upper end of the connecting member. The atomizing assembly is located below the connecting member 33. The connecting member 33 defines an air inlet passage 38 in its radial direction which extending through two opposite ends of the connecting member 33. Both ends of the air inlet passage 38 act as air inlets. An air adjusting ring 24 is sleeved around the outside of the connecting member 33 to cover the air inlet of the air inlet passage 38, and the air adjusting ring 24 can be adjusted to close or open the air inlet. An air inlet pipe 35 is located at the lower end of the connecting member 33 which communicates with the air inlet passage 38. The other end of the air inlet pipe 35 opposite to the connecting member 33 is connected to the atomizing assembly. A smoke pipe 34 is located within the air inlet pipe 35, wherein one end of the smoke pipe 34 extends to the upper end of the atomizing assembly, and the other end of the smoke pipe 34 connects with the cigarette holder 22. The inner cavity of the smoke pipe 34 constitutes a smoke passage, and the air inlet passage 38, the gap between the air inlet pipe 35 and the smoke pipe 34, and the smoke passage together constitute the air flow passage. The external air can flow to the upper end of the atomizing assembly through the air inlet, the air inlet passage 38 and the gap between the air inlet pipe 3 and the smoke pipe 34, and then flow out through the smoke passage and the cigarette holder 22 with the smoke generated by the atomizing assembly. In this embodiment, the inductive passage 39 communicates with the air inlet passage 38. Specifically, as shown in FIG. 7, one end of the inductive passage 39 extends through the connecting member 33 and then communicates with the air inlet passage 38.

As shown in FIG. 3, the arrangements of the components in the main support 46 is as follows: the atomizing assembly and the cigarette holder 22 are located in the left upper end of the main support 46, and the control board 21 and the inductive passage 39 are located in the right upper end of the main support 46. The battery assembly comprises a battery 27 and electrical connections for the components in the electronic cigarette, wherein the battery 27 is provided in the lower end of the main support 46. The above-described position arrangements can save space. It is more reasonable that the inductive passage 39 and the automatic trigger module 20 are located in the other side opposite to the atomizing assembly. Meanwhile, the independent position arrangement facilitates the mounting and detachment of the automatic trigger module 20 on the control board 21.

In one embodiment, the main support 46 can be made of plastic. The main support 46 defines a through hole 48, and the automatic trigger module 20 can pass through the through hole 48 and then be detachably mounted on the control board 21.

It can be appreciated that the electronic cigarette can further comprise the following conventional structures: an atomizer head 36 (as a part of the atomizing assembly described above) provided at the lower end of the air inlet pipe 35. An electrode tip 37 located at the lower end of the atomizer head 36 is configured to electrically connect to the battery 27 which supplies power to the atomizer head 36. The control board 21 activating the electronic cigarette mentioned above means that the control board 21 can control the battery 27 to supply power to the atomizer head 36 when the high potential signal from the sensor 11 is received. Once the user stops inhaling, the second end 112 of the sensor 11 communicate with the external air through the second vent hole 131, the inductive passage 39 and the cigarette holder 22, so that the second end 112 of the sensor 11 returns to an atmospheric pressure state. When the first end 111 and the second end 112 are both in an atmospheric pressure state, the sensor 11 stops output the high potential signal, and then the control board 21 controls the battery 27 to stop supplying power to the atomizer head 36.

In one embodiment, the electronic cigarette can further comprise a housing 44 having a mounting hole 45. The automatic trigger module 20 passes through the mounting hole 45 and is detachably mounted on the control board 21. The housing 44 functions as a package for the outside of the electronic cigarette.

In one embodiment, in order to reinforce the stability of the connection between the first connection 122 and the second connection 211, the electronic cigarette further comprises a rear cover 42. The rear cover 42 includes a receiving cavity configured to receive the automatic trigger module 20 and an air inlet opening 43 corresponding to the first vent hole 121. The automatic trigger module 20 is inserted into the receiving cavity and then is connected to the control board 21 through the mounting hole 45 together with the rear cover 42. A fixing structure is provided on the rear cover 42 to fix the rear cover 42 on the main support 46. The automatic trigger module 20 is fixed between the rear cover 42 and the control board 21.

Figure 5:
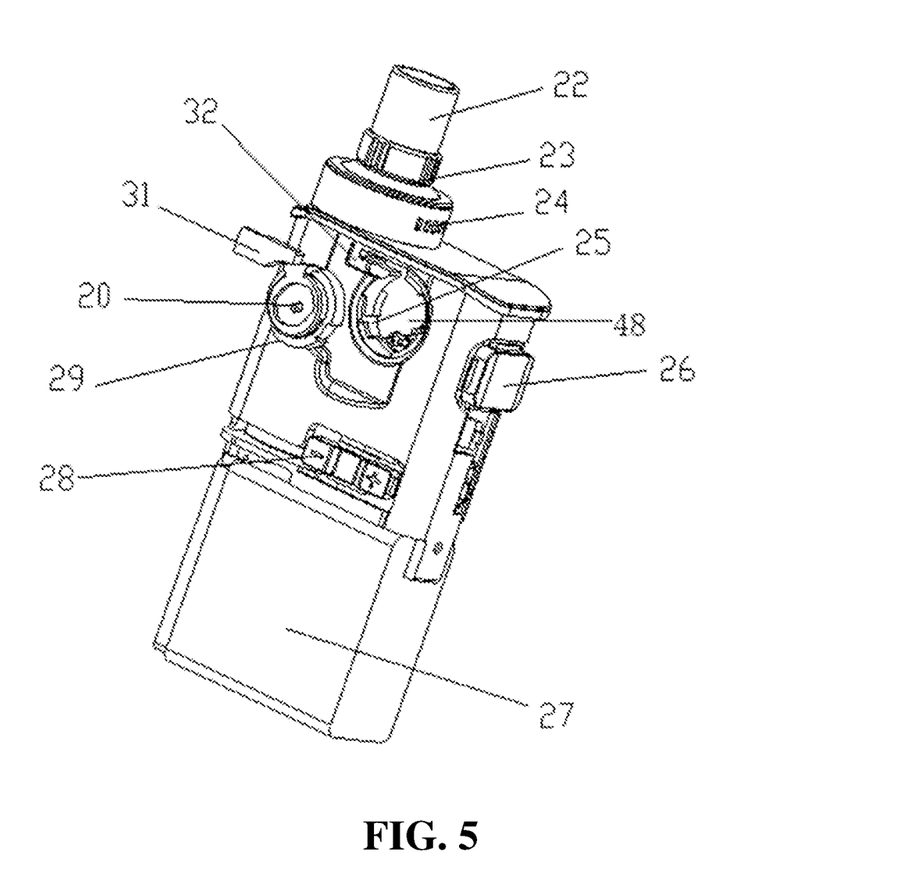
FIG. 5 is a perspective view of the electronic cigarette according to an embodiment of the present disclosure with the housing being removed.
Figure 6:
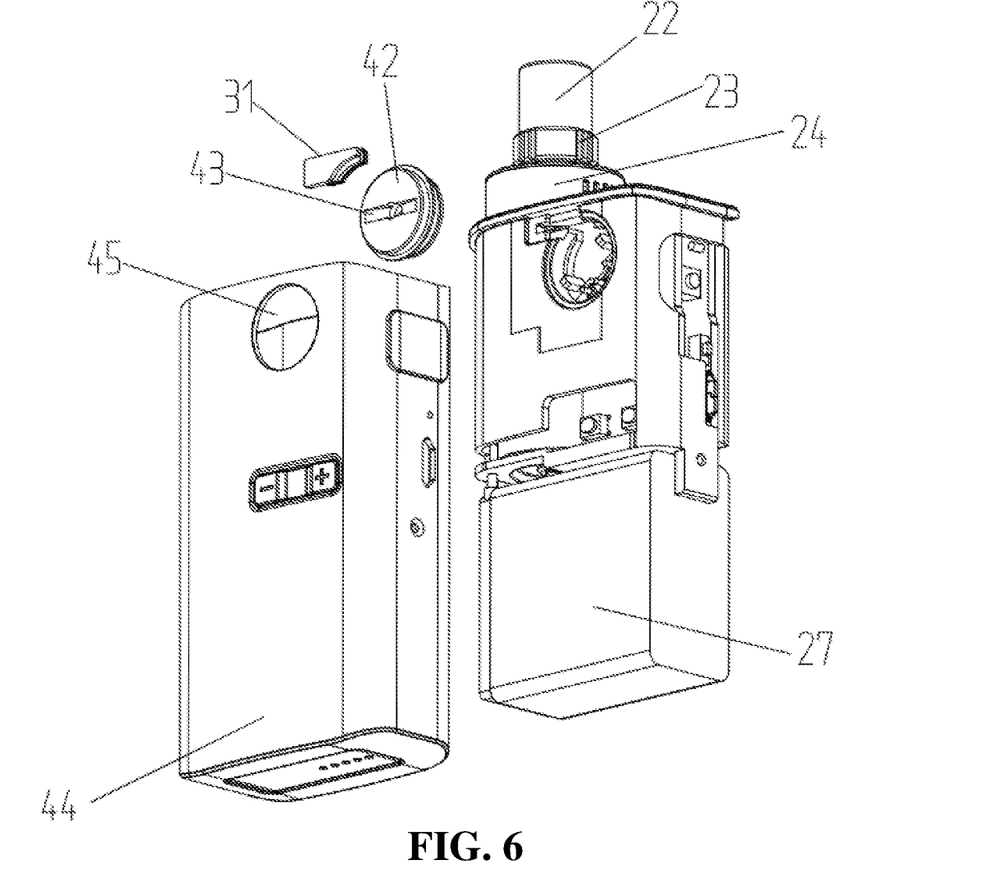
FIG. 6 is a partial exploded view of the electronic cigarette according to an embodiment of the present disclosure.

As shown in FIG. 5, in one embodiment, the fixing structure comprises a clamping ring 29 fixed outside the rear cover 42 and a clamping slot 25 defined on the wall of the through hole 48. The engagement between the clamping ring 29 and the clamping slot 25 has a positioning action during assembly, making the mounting of the automatic trigger module 20 more rapid, precise, and convenient. The fixing structure further comprises an insert block 31 and an insert block groove 32 which corresponding to the insert block 31. The insert block 31 is provided on the outside of the clamping ring 29, and the insert block groove 32 is provided on the main support 46.

It can be appreciated that, in other embodiments, the second connection 211 may not be provided on the control board 21. The second connection 211 can be provided on the main support 46 around the through hole 48, and can be electrically connected to the control board 21 via wires or other electrical components. It can be appreciated that, when the main support 46 is made of conducting materials, insulation sleeves should be provided between the second connection 211 and the main support 46. In addition to control the electronic cigarette to activate when accepts the high potential signal from the automatic trigger module 20, the control board 21 also can control the atomizing circuit and the power circuit.

In one embodiment, as shown in FIG. 3, the control board 21 is located in the right part of the main support 46. The main support 46 further includes a button 26 electrically connected to the control board 21. The button 26 and the automatic trigger module 20 both can control the operation of the electronic cigarette through a parallel circuit. When the automatic trigger module 20 is broken or removed, that is, when the circuit between the automatic trigger module 20 and the control board 21 is disconnected, the circuit between the control board 21 and the button 26 remains connected, and the activation of the electronic cigarette can be controlled via the button 26. Specifically, the button 26 is a standby power button, which can function as a temporary power button when the automatic trigger module 20 is broken or removed. The control board 21 can control the battery 27 to supply power to the atomizing assembly when the button 26 is pressed.

Alternatively, in one embodiment, the button 26 cooperates with the automatic trigger module 20 to control the activation of the electronic cigarette. Specifically, the button 26 is a security button, which prevents activating of the electronic cigarette caused by misoperation. That is to say, the control board 21 can activate the electronic cigarette only by pressing the button 26 and inhaling the electronic cigarette at the same time.

Alternatively, in one embodiment, the button 26 can be used as a standby power button and as a security button simultaneously.

In one embodiment, the control board 21 can further comprise an adjusting button 28, which is used to adjust the output power/output voltage from the battery 27 to the atomizing assembly.

The activating process of the electronic cigarette provided herein is: When the user sucks the cigarette holder 22, air is supplied into the electronic cigarette from the air inlet passage 38 of the electronic cigarette. At this time, a part of air in the inductive passage 39 can be brought into the air inlet passage 38, causing the inductive passage 39 in a negative pressure state. Meanwhile, since the second end 112 of the sensor 11 communicates with the inductive passage 39 through the second vent hole 131, the second end 112 is in a negative pressure state based on the mechanism of airflow. On the other hand, the first end 111 of the sensor 11 communicates with the external air through the first vent hole 121, so that the first end 11 is in a state of normal pressure. When the first end 111 and the second end 112 in different air pressure states, the sensor 11 can generate a high potential signal, which is then transmitted to the circuit board 12 of the electronic cigarette through the first connection 122 and the second connection 211, and then the circuit board 12 can activate the electronic cigarette according to the high potential signal. It will be appreciated that if the electronic cigarette is provided with a button 26 as a security button, the above-described function will not take effect unless the button 26 is pressed.

Therefore, the electronic cigarette provided in this embodiment adopts the automatic trigger module 20 which is detachably connected to the control board 21. Accordingly, the automatic trigger module 20 of the electronic cigarette is replaceable, which overcomes the problems in the prior art, and is suitable for wide application. Specifically, the automatic trigger module 20 of the electronic cigarette herein is provided with the first connection 122 and the via hole 132, and the control board 21 is provided with the second connection 211 which can pass through the via hole 132 and then abut against the first connection 122. The automatic trigger module 20 is detachably connected to the control board 21 through the cooperation of the second connection 211 and the via hole 132. The signal connection and electrical connection between the automatic trigger module 20 and the control board 21 are realized through the first connection 122 and the second connection 211 contacting with each other. When the user needs to detach the automatic trigger module 20, he or she just needs to withdraw the second connection 211 from the via hole 132. Therefore, the automatic trigger module 20 of the electronic cigarette according to the present disclosure is detachable, and can be easily detached and replaced.

Any combination made to various embodiments of the present disclosure without departing from the spirit of the disclosure should be regarded as the disclosure of the present disclosure; various simple modifications made to the technical solution or any combination made to the various embodiments without violating the technical spirit of the disclosure is intended to be within the scope of the present disclosure.

The invention claimed is:

1. An automatic trigger module used for an electronic cigarette, comprising:
    a sensor, having a first end and a second end which are opposite to each other;
    a circuit board, having a first vent hole communicating with the first end and a first connection; and
    a sealing seat, having a second vent hole communicating with the second end,
    wherein the first end is located on the circuit board, and the second end is located in the second vent hole.

2. The automatic trigger module according to claim 1, wherein the sealing seat defines a via hole corresponding to the first connection.

3. The automatic trigger module according to claim 1, wherein the first connection is a contact dot, a contact post or a contact sheet.

4. An electronic cigarette, comprising:
    an automatic trigger module, comprising:
        a sensor, having a first end and a second end which are opposite to each other;
        a circuit board, having a first vent hole communicating with the first end of the sensor and a first connection;
        a sealing seat, having a second vent hole communicating with the second end; and
    a control board, having a second connection,
        wherein the first end is located on the circuit board, and the second end is located in the second vent hole, and
    wherein the automatic trigger module is detachably connected to the control board, and when the automatic trigger module is connected to the control board, the first connection and the second connection contact with each other to realize a transmission of signal.

5. The electronic cigarette according to claim 4, wherein the sealing seat defines a via hole corresponding to the first connection.

6. The electronic cigarette according to claim 4, wherein the first connection is a contact dot, a contact post or a contact sheet.

7. The electronic cigarette according to claim 4, wherein the second connection is a contact dot, a contact post or a contact sheet.

8. The electronic cigarette according to claim 4, further comprising an inductive passage and a cigarette holder, wherein one end of the inductive passage communicates with the second vent hole and the other end of the inductive passage communicates with the cigarette holder.

9. The electronic cigarette according to claim 4, further comprising a housing defining a mounting hole for the automatic trigger module to pass through when mounting or removing.

10. The electronic cigarette according to claim 4, further comprising a rear cover defining a receiving cavity configured to receive the automatic trigger module and an air inlet opening corresponding to the first vent hole, wherein the automatic trigger module is received in a space formed by the receiving cavity and the control board.

11. The electronic cigarette according to claim 10, further comprising a main support defining a through hole, wherein the automatic trigger module passes through the through hole and then is detachably connected to the control board.

12. The electronic cigarette according to claim 11, further comprising:
    a clamping ring located on an outside of the rear cover, and
    a clamping slot defined on a wall of the through hole,
    wherein the rear cover is fixed on the main support through cooperation of the clamping ring and the clamping slot.

13. The electronic cigarette according to claim 12, further comprising:

an insert block located on an outside of the clamping ring, and an insert block groove defined on the main support, wherein the insert block is engaged with the insert block groove.

14. The electronic cigarette according to claim 4, further comprising a button, wherein the button is a standby power button and/or a safety protection button.

\* \* \* \* \*